United States Patent [19]

Kikuchi et al.

[11] 4,229,167
[45] Oct. 21, 1980

[54] DOWEL PIN SETTING INSTRUMENT

[75] Inventors: Makoto Kikuchi; Keijyu Yamada, both of Tokyo, Japan

[73] Assignee: Porceny Co., Ltd., Tokyo, Japan

[21] Appl. No.: 921,049

[22] Filed: Jun. 30, 1978

[30] Foreign Application Priority Data

Apr. 12, 1978 [JP] Japan .......................... 53/47109[U]

[51] Int. Cl.³ .............................................. A61C 19/00
[52] U.S. Cl. ..................................................... 433/74
[58] Field of Search .................... 32/11, 40 R; 433/74

[56] References Cited

U.S. PATENT DOCUMENTS

| 2,836,849 | 6/1958 | Humphrey | 32/11 |
| 3,255,992 | 6/1966 | Kersten | 32/11 |
| 3,469,316 | 9/1969 | Stern et al. | 32/40 R |
| 3,552,018 | 1/1971 | Zahn | 32/40 R |
| 3,553,839 | 1/1971 | Gores | 32/11 |
| 3,639,985 | 2/1972 | Pasko | 32/11 |
| 3,717,933 | 2/1973 | Charron | 32/11 |
| 3,753,291 | 8/1973 | Bocian et al. | 32/11 |
| 4,001,938 | 1/1977 | Cooper | 32/11 |

FOREIGN PATENT DOCUMENTS

| 2267742 | 11/1975 | France | 32/11 |
| 51-120093 | 10/1976 | Japan | 32/11 |

Primary Examiner—Louis G. Mancene
Assistant Examiner—John J. Wilson

[57] ABSTRACT

A dowel pin setting instrument provided with a supporting means having a first member and a second member detachably inserted into the first member so as to prevent its rotation therein and mounted on an impression material other than a tooth mark and a flexible tube having dowel pin fitted at one end thereto and coupled at the other end to supporting means.

18 Claims, 17 Drawing Figures

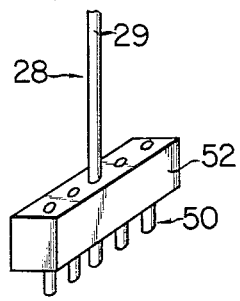
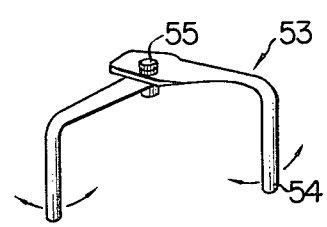
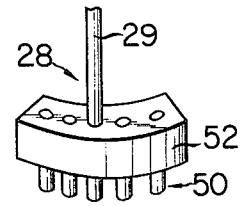
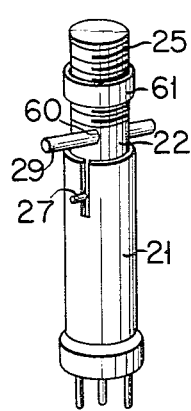
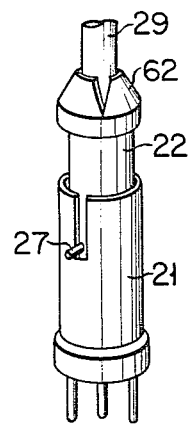
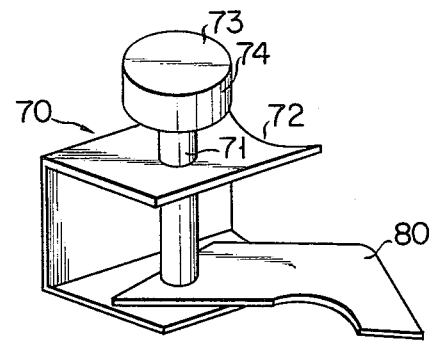
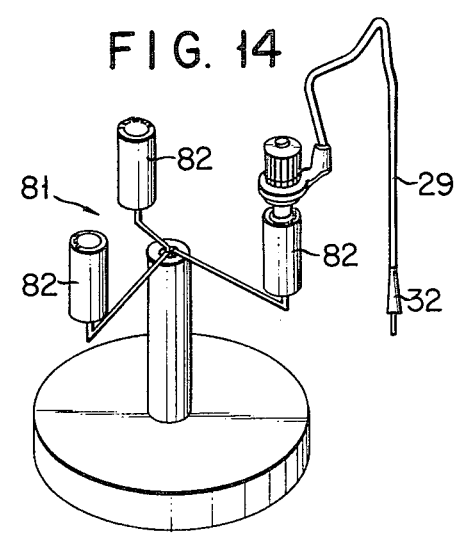
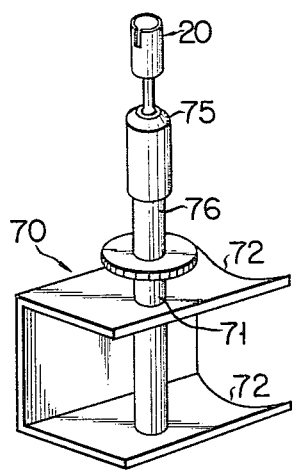
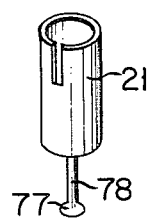
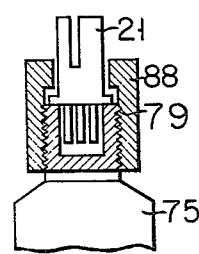
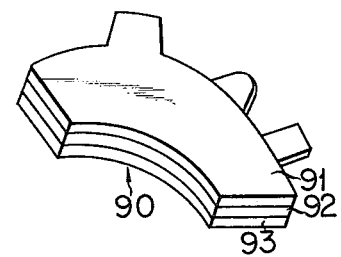

DOWEL PIN SETTING INSTRUMENT

BACKGROUND OF THE INVENTION

The present invention relates to a dowel pin setting instrument.

In preparing a tooth-mark mold, when the tooth-mark mold is filled with primary plaster, it is generally necessary to set a dowel pin in the primary plaster forming the tooth mark mold. Various dowel pin setting instruments have been developed and put into practical use. One of them is disclosed in Japanese Patent Application No. 50-44845 invented by the inventor of the present application. As shown in FIG. 1, the dowel pin setting instrument 1 in the patent application is provided with a support A having a rod 3 with a plurality of legs 2 at the bottom, a sleeve 6 detachably fitted into the rod 3 and a plurality of segmental spaces defined by partition plates 4 and filled with wax 5, a holder 8 for holding a bar 7 having a dowel pin fitted thereinto, and a frame B made of a wire which fixes the holder 8 and provided at one end with a handle 9 for opening and closing the holder 8 and at the other end with a post 10 planted in the wax 5 filled the segmental spaces of the sleeve 6.

The dowel pin setting instrument is advantageous in that it is possible to easily set the dowel pin at a desired location on the tooth-mark mold. However, this setting instrument still suffers from some problems. First it requires work to attach the bar with the dowel pin to the holder fixed on the frame on all such occasions. The second problem is that it is necessary to remove the post of the frame from the wax and again position the post into the wax so as to be located at a desired portion of the tooth-mark.

SUMMARY OF THE INVENTION

Accordingly, an object of the invention is to provide a dowel pin setting instrument capable of setting a dowel pin at a desired position of the tooth-mark mold in a simple and rapid manner.

BRIEF DESCRIPTION OF THE DRAWINGS

FIGS. 4, 5 and 7 show perspective views of modifications of the dowel pin holder used in a dowel pin setting instrument according to the invention;

FIG. 6 shows a perspective view of a parallel-keeping jig for the holder of FIG. 5;

FIGS. 8 and 9 show a perspective view of modifications of a coupling means used in the dowel pin setting instrument according to the invention;

FIGS. 10 and 11 show perspective views of other examples of the fixing means for fixing the dowel pin holder used in the dowel pin setting instrument according to the invention;

FIG. 12 shows a perspective view of another example of a sleeve of the supporting member used in the fixing means shown in FIG. 11;

FIG. 13 shows a side elevation view of still another example of the sleeve shown in FIG. 12;

FIG. 14 shows a perspective view of a stand for holding a tubular rod having a flexible bushing with a dowel pin inserted therein;

FIG. 15 shows a perspective view of a pin holder enabling the dowel pin to be easily removed from a secondary plaster.

DESCRIPTION OF THE PREFERRED EMBODIMENTS

Figure 2:
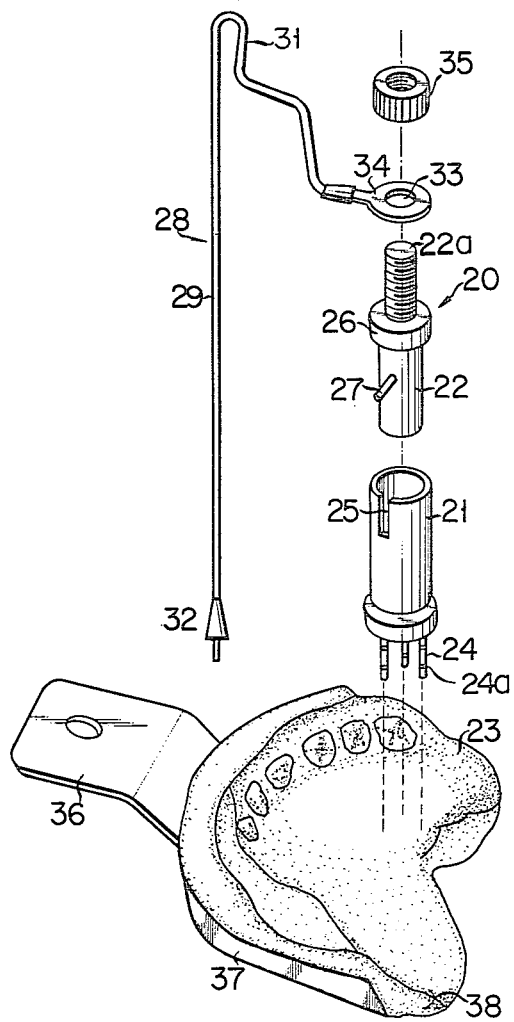
FIG. 2 shows a partial exploded-perspective view of a dowel pin setting instrument according to the invention.
Figure 3:
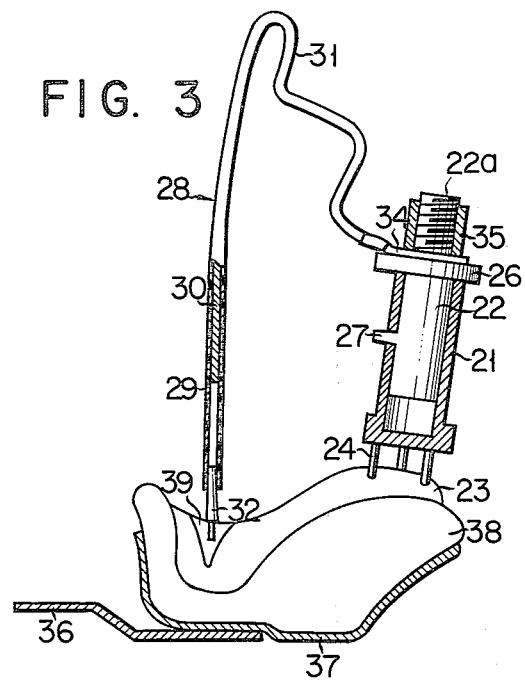
FIG. 3 shows a cross sectional view of the same in FIG. 1.
Figure 4:
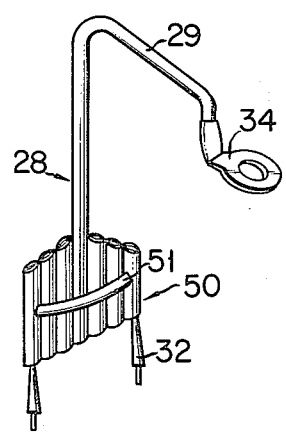

To explain in detail the invention, reference is now made to FIGS. 2 and 3 illustrating an embodiment of a dowel pin setting instrument according to the invention. As indicated in the figures, a support generally designated by reference numeral 20 is provided with a sleeve or tubular body 21 and a rod 22 to be inserted into the tubular body 21. The support 20 is set in an impression material area 23 made of primary resilient material as shown in FIG. 2. The tubular body 21 is hollow and provided at the bottom with a plurality of legs 24 and at the side wall with a slit 25 elongated downwardly from the top periphery thereof. The legs 24 are set in a desired location of the part of the impression material 23 of resilient material except the tooth mark part. A plurality of grooves 24a are formed in the legs 24. The rod 22 includes a threaded part 22a at the upper portion thereof, an enlarged ring-like stopper 26 at the middle position thereof, and a projection 27 radially projecting on the lower part of the rod 22. When the rod 22 is inserted into the tubular body 21, the projection 27 progresses along the slit 25 of the tubular body 21 to finally come into engagement with the bottom end of the slit 25.

A dowel pin holder 28 to support a dowel pin 32 comprises a tube 29 made of flexible material such as plastic. The flexible tube 29 includes therein a flexible metal such as a core wire 30 made of lead and fuse with one end disposed slightly apart from the top end of the tube 29. The tube 29 including the core wire 30 is bent to form a grip portion 31 so as to easily flex its shape by hand. The dowel pin 32 is fitted into the space extending from the top end of the tube 29 to the terminal of the core wire. Fixed at the other end of the tube 29 is a flat ring 34 with a hole 33 to be set around the threaded part 22a of the rod 22. A screw shown at 35 is used to fix the flat ring against the stopper 26.

Generally, the impression material is so constructed that a primary impression material 38 is mounted on a tray holder (an impression tray) 37 with a grip 36 and then a secondary impression material 23 is mounted on the primary impression 38. The impression material may be a dental impression material with the same material as the former.

In operation, the primary and secondary impression materials 38 and 23 are first mounted on the tray holder 37. A dentist grasps the grip 36 of the tray holder 37 with one hand and presses the secondary impression material 23 against the tooth of a patient to form a duplication of the tooth in the secondary impression material 23. A case of shaping duplications of teeth will be referred to later. Then, the legs 24 provided at the bottom of the support 20 are planted in the secondary impression material 23 at desired positions other than a tooth mark, with the flexible tube 29 fitted with the dowel pin 32 being tightly screwed on the support 20. While raising the tray 37 with the impression material layered thereon with one hand holding the sleeve 21 and the stopper 26, the dentist grasps the grip 31 of the tube 29 with the other hand and moves the forward part of the tube 29 with the dowel pin 32 attached thereto by using the flexibility of the core wire 30 inserted in the flexible tube 29, thereby to bring the top end of the tube 29 to the expected position in the tooth mark. In this condition, it is checked as to whether the dowel pin 32 is located at a desired position of the tooth mark. After this checking, the tray 37 is horizontally placed and, holding again the stopper 26 with one hand, the rod 22 having the tube 29 attached thereto with the dowel pin 32 fitted thereinto is pulled out from the sleeve 21. In pulling out the rod 29, care must be taken so as not to deform the tube 29 and shift the sleeve 21 from the set position. Then, the primary plaster 39 is caused to flow into the tooth mark portion, after the dowel pin is pulled out. Then, before the primary plaster hardens, the rod 22 with the tube 29 is fitted again into the sleeve 21, sliding the projection 27 along the slit 25, so as not to shift the sleeve 21 from the set position, and the dowel pin is inserted into the primary plaster region 39 in the tooth mark area.

Figure 1A:
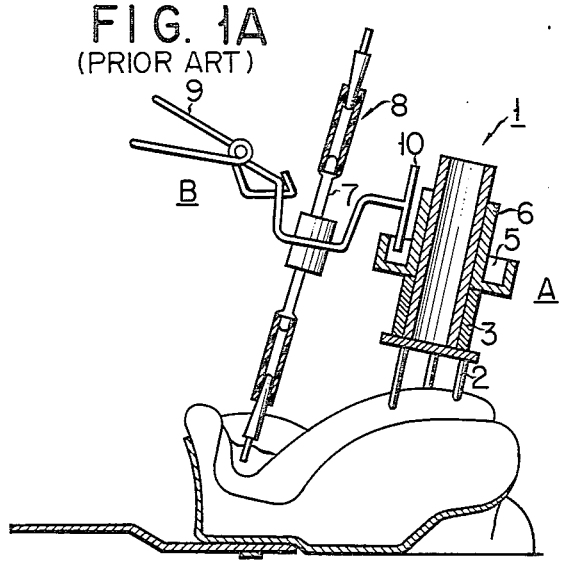
FIG. 1A shows a cross sectional view of a prior art dowel pin setting instrument.
Figure 1B:
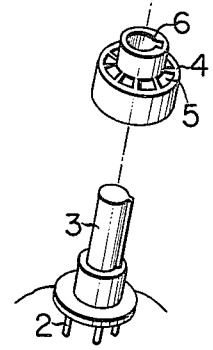
FIG. 1B shows a perspective view of a supporting member shown in FIG. 1.
Figure 16:
FIG. 16 shows a perspective view of a moulded tooth prepared by using the dowel pin setting instrument according to the invention.

After the primary plaster hardens, the legs 24 of the sleeve 21 are pulled out from the impression material 23 with one hand holding the sleeve 21, and the tube 29 is separated from the dowel pin 32 planted in the primary plaster 39. As a result, the dowel pin 32 is set upright with one half buried in the plaster and the other half projecting from the plaster. Following this, a parting agent is coated on the primary impression material around the dowel pin and a pin holder 90 to be described later is put on the dowel pin. In this condition, the secondary plaster 41 is poured onto the primary plaster 39. After the secondary plaster 41 hardens, the plaster portion is separated from the tooth mark portion of the impression material and the primary plaster 39 of the tooth mark to be formed is cut deep thereinto from both sides and the pin holder 90 put on the dowel pin 32 is removed from the secondary plaster 41. Then, the projecting end of the dowel pin 32 is pushed through a hole made in the secondary plaster by the pin holder 90 so that a desired moulded tooth 100 as shown in FIG. 16 is obtained.

The above-mentioned example relates to the case to set a single dowel pin. The explanation to follow is the case for setting a plurality of dowel pins.

A plurality of pin holders 28 are fixed to rods 22 by the above-mentioned means. The dowel pins 32 attached to the pin holders 28 respectively are disposed at a desired tooth portion by using a flexible metal member 30. This may be performed in ways as shown in FIGS. 4 to 7. As shown, the flexible tube 29 is coupled at one end together with a plurality of additional plastic tubes 50 disposed in parallel to each other to allow dowel pins to be inserted. These tubes are coupled with a lead tube 51 disposed normal to the tubes. In FIGS. 5 to 7, the plastic tubes 50 are fitted in holes formed in series and in parallel at given intervals in a block like member 52 made of, for example, hard plastic or light alloy such as aluminum. The parallel holes may be substituted by a plurality of semi-grooves formed so as to permit the plastic tubes to be fitted thereon. When the teeth marks to be formed are located on only one side of a teeth arrangement of an object, a necessary number of dowel pins 32 are fitted into the corresponding tubes 50. When the teeth marks to be formed are located on both sides of the teeth arrangement, the pin holders disposed on the sides must be disposed in parallel. The reason for this is that the teeth marks with dowel pins planted must be simultaneously fitted and removed. It is preferable to use a parallel-keeping jig 53 as shown in FIG. 6 to ensure the parallel arrangement of the pin holders. The jig 53 is inserted into one end of respective suitable tubes 50. The jig 53 has two legs 54 each having an end which is rotatably coupled to each other by means of a pin joint 55. When a plurality of teeth marks of the front teeth are formed, the plastic block 52 shaped corresponding to the front teeth arrangement or a lead-included tube 51 is used according to it.

From the foregoing, it will be seen that the pin holder thus constructed enables a plurality of desired teeth marks to simultaneously be formed.

Modifications of the dowel pin setting instrument shown in FIGS. 2 and 3 will now be given.

In the above-mentioned embodiment, the rod 22 is inserted into the sleeve 21. Conversely, it may be so designed that the sleeve 21 is inserted into the rod 22. The combination of the slit 25 of the sleeve 21 and the projection 27 of the rod 22 prevents the rod 22 from rotating in the sleeve 21. Also, the sleeve 21 and the rod 22 may be formed polygonally. In that case, the rotation of the rod 22 may be prevented without using the combination of the silt and projection.

The flexible pin holder 28 may be fixed to the rod 22 of the supporter 20 by passing one end of the tube 29 into a hole 60 formed in the lower portion of the rod 22 and to tightly screw it by a screw 61, as shown in FIG. 8, or by holding one end of the tube 29 in a slit cone chuck 62 as shown in FIG. 9.

When fixed at a desired portion other than the tooth mark, the support 20 may be provided on an impression material, if the impression material is made of resilient material, or material having a strong holding force. In that case, the fixing means for it may be a plurality of, preferably three, legs with sharp points provided at the bottom of the sleeve 21 of the support 20. When the impression material is not hard or has a weak holding force such as gelatinous material, the legs are ineffective for the fixing means, and an auxiliary holder 70 as shown in FIGS. 10 and 11 is used. The auxiliary holder 70 is mounted to the grip 36 of the tray holder 37. The holder 70 is channel shaped and provided with a threaded hole 71 formed in the top flange thereof, and has a semi-circular arc groove 72 formed at one end thereof. A member 74 having a head at the top end of resilient material such as rubber is screwed into the hole 71, as shown in FIG. 10. The support 20 with legs 24 at the bottom is thrust into the resilient material. Alternately, a bar 76 with a universal joint 75 may be screwed into the screw hole 73, as shown in FIG. 11. The support 20 is fixed on the universal joint 75. In this case, attached to the bottom of the sleeve 21 is a bar 78 of which the end has a ball like portion 77, as shown in FIG. 12. Alternately, the joint 75 is provided at the outer surface with a threaded portion 79 and the sleeve 21 with the legs 24 may be fixed onto the joint 75 by means of a screw 88 (FIG. 13). A plurality of the auxiliary holders of this kind may be used. In this case, the auxiliary holder 70 as shown in FIG. 10 is attached to a plate 80.

When the flexible tube 29 is pulled out from the sleeve 21 of the support 20, together with the rod 22, it is preferable to insert the rod 22 connected with the tube 29 having the dowel pin 32 into a rod holder 82 of a stand 81 as shown in FIG. 14, for the purpose of preventing the tube being pulled out from being deformed.

FIG. 15 shows a perspective view of a pin holder 90 used when the teeth mark with the setting dowel pin is separated from the secondary plaster. The pin holder 90 comprises three plates 91 to 93. The top and bottom plates 91 and 93 are made of sponge with iron plates attached thereto. The middle plate 92 is made of a magnet. These plates are coupled together by the magnetic force of the plate 92.

As described above, in the dowel pin setting instrument according to the invention, a dowel pin is inserted into a flexible tube so that the dowel pin may easily be positioned to a desired tooth mark. Additionally, the attachement and removal of the support may easily be conducted so that the handling of the machine is simplified.

What we claim is:

1. A dowel pin setting instrument to be attached on an impression material comprising a flexible tube adapted for fitting a dowel pin at one end;
   a flexible core wire coaxially inserted in said tube;
   supporting means comprising a sleeve having an opening at one end and a rod for insertion into the opening in the sleeve;
   engaging means for engaging the rod to the sleeve to prevent the rotation of the rod in a peripheral direction relative to the sleeve when the rod is inserted into the sleeve, and disengaging the rod from the sleeve when the rod is removed from the opening in the sleeve;
   connecting means for connecting the other end of the flexible tube to the rod; and
   fixing means for fixing the sleeve at its other end at a portion other than a tooth mark formed on the impression material.

2. A dowel pin setting instrument according to claim 1 wherein said engaging means comprises a slit formed at said one end of the sleeve and a projection formed on the periphery of the rod and slidably insertable into the slit when the rod is inserted into the opening in the sleeve.

3. A dowel pin setting instrument according to claim 1, in which said impression material comprises a secondary impression material.

4. A dowel pin setting instrument according to claim 1, in which said fixing means comprises a plurality of pins having grooves at the outsides thereof attached to the said other end of said sleeve, said supporting means being fixed by thrusting said pins into said impression material.

5. A dowel pin setting instrument according to claim 1, in which said supporting means is mounted on a tray holder carrying said impression material thereon.

6. A dowel pin setting instrument according to claim 5, in which said tray holder includes auxiliary means for mounting said supporting means.

7. A dowel pin setting instrument according to claim 6, in which said auxiliary means comprises a soft resilient member.

8. A dowel pin setting instrument according to claim 6, in which said auxiliary means comprises a universal joint.

9. A dowel pin setting instrument according to claim 1, in which said flexible tube is a vinyl tube.

10. A dowel pin setting instrument according to claim 9, in which said flexible tube has a grip to enable it to be grasped easily by hand.

11. A dowel pin setting instrument according to claim 1, in which said flexible wire is made of lead.

12. A dowel pin setting instrument according to claim 1, in which said flexible core wire is disposed apart from the one end of said flexible tube so as to permit a dowel pin to be fitted thereinto.

13. A dowel pin setting instrument according to claim 1, in which said flexible tube has at the one end a plurality of additional tubes disposed in parallel to each other.

14. A dowel pin setting instrument according to claim 13, in which said flexible tubes are kept parallel by using a parallel-keeping jig with legs inserted into said respective additional tubes.

15. A dowel pin setting instrument according to claim 13, in which said additional tubes are curved corresponding to the curve of anterior teeth.

16. A dowel pin setting instrument according to claim 1, in which said rod and sleeve are polygonally formed so as to fit each other.

17. A dowel pin setting instrument according to claim 1, in which said connecting means between said rod and said flexible tube comprises a flat ring attached to the other end of said flexible tube, a threaded portion formed on said rod around which said ring can be placed, and a screw for said threaded portion fastening said ring to said rod.

18. A dowel pin setting instrument according to claim 1, in which said connecting means between said rod and said flexible tube comprises a split cone chuck on said rod for receiving the other end of the flexible tube.

* * * * *